(12) United States Patent
Zhang

(10) Patent No.: US 12,376,823 B2
(45) Date of Patent: Aug. 5, 2025

(54) FETAL MOVEMENT DETECTION METHOD FROM DOPPLER ULTRASOUND SIGNAL

(71) Applicant: KONINKLIJKE PHILIPS N.V., Eindhoven (NL)

(72) Inventor: Ying Zhang, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 16/640,531

(22) PCT Filed: Aug. 9, 2018

(86) PCT No.: PCT/EP2018/071592
§ 371 (c)(1),
(2) Date: Feb. 20, 2020

(87) PCT Pub. No.: WO2019/038097
PCT Pub. Date: Feb. 28, 2019

(65) Prior Publication Data
US 2024/0415487 A1 Dec. 19, 2024

(30) Foreign Application Priority Data

Aug. 23, 2017 (WO) ................. PCT/CN2017/098594
Oct. 3, 2017 (EP) ..................................... 17194499

(51) Int. Cl.
*A61B 8/08* (2006.01)
*A61B 8/00* (2006.01)

(52) U.S. Cl.
CPC ............ *A61B 8/0866* (2013.01); *A61B 8/488* (2013.01)

(58) Field of Classification Search
CPC .............................. A61B 8/0866; A61B 8/488
See application file for complete search history.

(56) References Cited

U.S. PATENT DOCUMENTS

| 5,666,959 A | 9/1997 | Deans et al. |
| 5,954,653 A | 9/1999 | Hatfield et al. |

(Continued)

FOREIGN PATENT DOCUMENTS

| CN | 102048558 A | 5/2012 |
| CN | 103190913 A | 7/2013 |

(Continued)

OTHER PUBLICATIONS

International Search Report and Written Opinion, International Application No. PCT/EP2018/071592, Mailed on Dec. 4, 2018.

(Continued)

*Primary Examiner* — Dixomara Vargas

(57) ABSTRACT

A method (100) of detecting fetal movements includes: deriving a plurality of peaks from the Doppler ultrasound signal acquired from a subject, each peak of the plurality of peaks being associated with an envelope of a signal segment of the Doppler ultrasound signal; calculating a density of the peaks as a function of a plurality of amplitude grids, the density indicating the number of peaks with amplitude in each amplitude grid; selecting a fetal movement threshold based on the calculated density, and determining whether a signal segment of the Doppler ultrasound signal includes a fetal movement by comparing the amplitude of the peak associating with the envelope of the signal segment with the fetal movement threshold.

16 Claims, 4 Drawing Sheets

(56) References Cited

U.S. PATENT DOCUMENTS

| | | | |
|---|---|---|---|
| 8,353,836 B2 | 1/2013 | Azuma | |
| 9,636,081 B2 | 5/2017 | Reuter | |
| 2008/0119736 A1 | 5/2008 | Dentinger | |
| 2009/0012432 A1* | 1/2009 | Sharf | A61B 5/1116 |
| | | | 600/588 |
| 2009/0270767 A1 | 10/2009 | Nishihara et al. | |
| 2013/0158406 A1* | 6/2013 | Kabakov | A61B 8/02 |
| | | | 600/453 |
| 2013/0158407 A1* | 6/2013 | Kabakov | A61B 8/0866 |
| | | | 600/453 |
| 2014/0378855 A1 | 12/2014 | Dash et al. | |
| 2016/0058363 A1 | 3/2016 | Hayes-Gill et al. | |
| 2021/0298610 A1* | 9/2021 | Hocking | A61B 5/02028 |

FOREIGN PATENT DOCUMENTS

| | | |
|---|---|---|
| RU | 2353290 C2 | 4/2009 |
| WO | 1990000368 A1 | 1/1990 |
| WO | 1993019666 A2 | 10/1993 |
| WO | 2015062851 A1 | 5/2015 |

OTHER PUBLICATIONS

Chen, W. et al., "A comparison of the fragmentation thresholds and inertial cavitation doses of different ultrasound contrast agents", The Journal of the Acoustical Society of America, vol. 113, No. 1, Jan. 2003.

Wrobel, J. et al., "Automated Detection of Fetal Movements in Doppler Ultrasound Signals Versus Maternal Perception", Journal of Medical Informatics and Technologies, vol. 23, Jan. 2014.

Endres, D. et al., "Modelling spike trains and extracting response latency with Bayesian binning", Journal of Physiology—Paris, 2010.

Jezewski, M. et al., "Analysis of Extracted Cardiotocographic Signal Features to Improve Automated Prediction of Fetal Outcome", Biocybernetics and Biomedical Engineering, 2010, vol. 30, No. 4, pp. 29-47.

* cited by examiner

FETAL MOVEMENT DETECTION METHOD FROM DOPPLER ULTRASOUND SIGNAL

This application is the U.S. National Phase application under 35 U.S.C. § 371 of International Application No. PCT/CN2017/098594, filed on 23 Aug. 2017, which claims the benefit of European Application Serial No. 17194499.4, filed 3 Oct. 2017. These applications are hereby incorporated by reference herein.

FIELD OF THE INVENTION

The following relates generally to the Doppler ultrasound arts, fetal monitoring arts, fetal movement monitoring arts, and related arts.

BACKGROUND OF THE INVENTION

The use of a fetal monitor employing Doppler ultrasound for detecting fetal movements is known, e.g. Wrobel et al., "Automated Detection of Fetal Movements in Doppler Ultrasound Signals versus Maternal Perception", J. of Medical Informatics & Technologies vol. 23 pp. 43-50 (2014). In the approach of Wrobel et al., the Doppler ultrasound amplitude versus time signal is initially low pass-filtered to identify and remove higher frequency components attributable to fetal heart beats. The resulting low pass-filtered signal is referred to as a continuous actogram, as it is continuous and is expected to principally capture fetal movements. Data are processed in one second segments, with each segment being labeled as a movement if the number of samples exceeding a threshold exceeds a limit value. This converts the continuous actogram to a binary actogram.

Wrobel et al. employs an actively adapted threshold generated as follows. The threshold is initially set to a low value. Thereafter, each 1 sec segment is processed to identify the mean value over the last 25% of the one second segment. The threshold is adapted to half of this mean value, unless that is lower than the initial minimum threshold in which case the latter is selected. The approach of Wrobel et al. for threshold selection has certain difficulties. It assumes a certain distribution of the clinical data that may limit the application of the method as it may or may not be suitable for a particular patient.

Therefore, it is desired for improved system and method for fetal movement detection.

SUMMARY OF THE INVENTION

In one disclosed aspect, a method of detecting fetal movements is disclosed. A plurality of peaks is derived from a Doppler ultrasound signal acquired from a fetus. A density of the peaks as a function of peak amplitude is calculated. A fetal movement threshold is selected based on the calculated density of the peaks. It is determined whether a Doppler ultrasound signal segment under test includes a fetal movement by comparing the amplitude of a peak derived from the Doppler ultrasound signal segment under test with the fetal movement threshold.

In another disclosed aspect, a device for detecting fetal movements includes a Doppler ultrasound device including a Doppler ultrasound transducer for acquiring Doppler ultrasound signal from a fetus. At least one electronic processor is programmed to derive a plurality of peaks from the Doppler ultrasound signal, calculate a density of the peaks as a function of peak amplitude, and select a fetal movement threshold based on the calculated density of the peaks. In some embodiments, the fetal movement threshold is selected as the peak amplitude at which the density of the peaks is maximum. The peak amplitude at which the density of the peaks is maximum may be identified, for example, by binning the plurality of peaks into peak amplitude bins and identifying the peak amplitude of the peak amplitude bin containing the largest number of peaks. In some embodiments the least one electronic processor is further programmed to segment the Doppler ultrasound signal to identify a Doppler ultrasound signal segment under test, and to determine whether the Doppler ultrasound signal segment under test includes a fetal movement by comparing the amplitude of a peak derived from the Doppler ultrasound signal segment under test with the fetal movement threshold.

One advantage resides in determining true fetal movements.

Another advantage resides in improved discrimination between true fetal movements and false fetal movements.

Another advantage resides in providing a fetal movement threshold for detecting fetal movements that is tuned to the fetus under test.

Another advantage resides in providing one or more of the foregoing benefits with improved computational efficiency.

Another advantage resides in providing one or more of the foregoing benefits automatically, without relying upon subjective sensing of fetal movement by the mother.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various operations and arrangements of operations. The drawings are only for purposes of illustrating the preferred embodiments and are not to be construed as limiting the invention.

DETAILED DESCRIPTION OF EMBODIMENTS

The following discloses an improved approach for adaptation of a threshold used for fetal movement detection in a fetal monitor employing Doppler ultrasound. The threshold is determined automatically by a Doppler ultrasound system without the need for human intervention. To do so, a plurality of peaks are calculated from a Doppler ultrasound signal. A density of the peaks as a function of peak amplitude is determined, and then a fetal movement threshold is selected as a peak amplitude with highest calculated density. Movements are identified as Doppler ultrasound signal peaks whose amplitudes are above the selected movement threshold.

Advantageously, the fetal movement threshold is determined without reference to any inputs from the mother. By comparison, in some other approaches the mother provides training labels, for example by pressing a button when she senses a fetal movement. While such data are contemplated as additional training information or for use in verification of the fetal movement threshold, the disclosed approach for selecting the fetal movement threshold does not rely upon such inputs from the mother. This is beneficial since the mother's sensing of fetal movements is subjective and sometimes may be in error.

Figure 1:
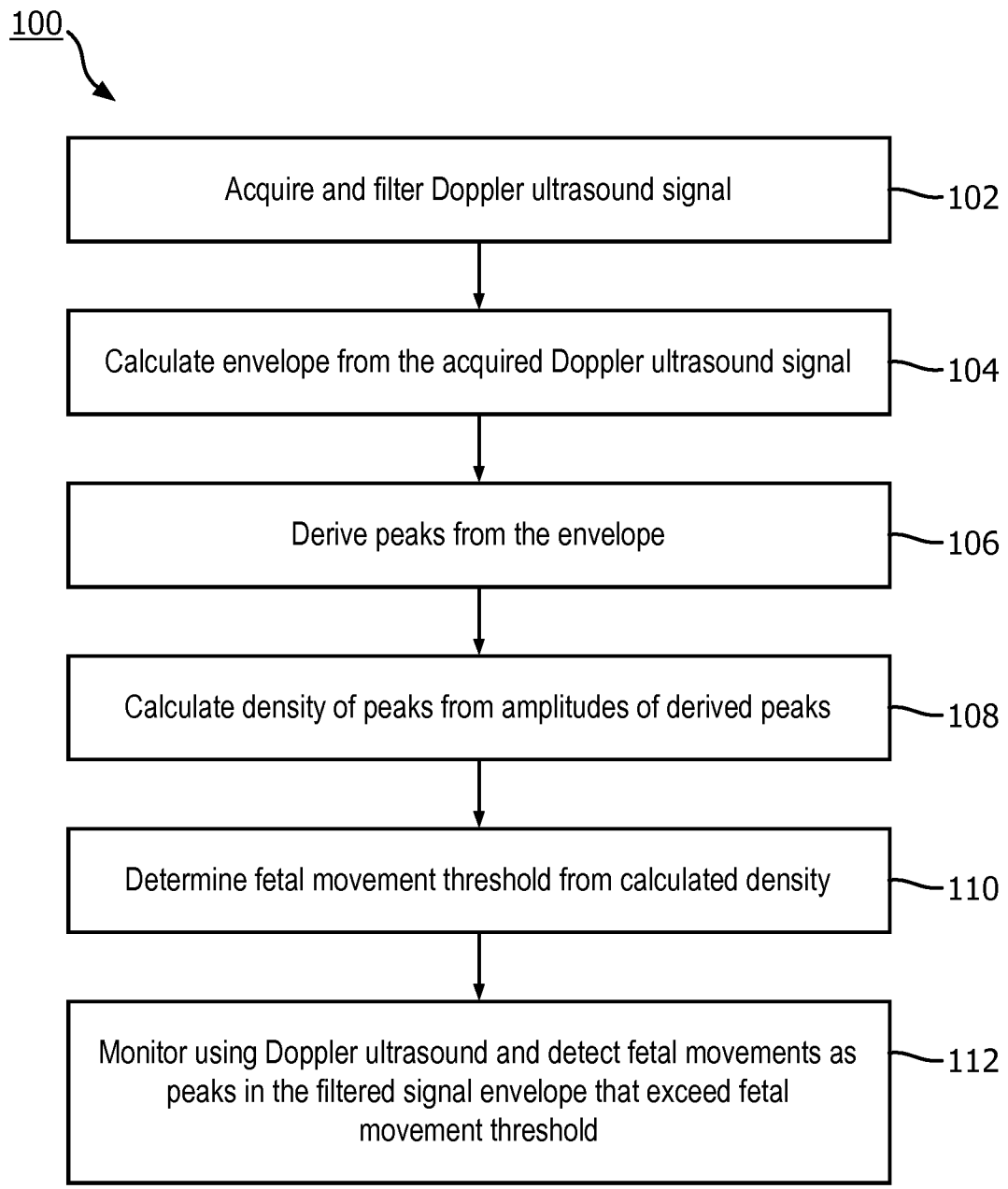
FIG. 1 shows an exemplary flow chart operation a fetal movement detection method.

With reference to FIG. 1, an illustrative embodiment of the fetal movement detection method 100 is diagrammatically shown as a flowchart. At 102, a Doppler ultrasound signal is acquired. For example, the Doppler ultrasound signal is sampled at a predetermined sampling rate or period (e.g., a sample acquired every 25 milliseconds). During the ultrasound signal acquisition 102, an ultrasound transducer is placed over an abdomen area of a mother, positioned so as to sonicate the infant in the womb. In some examples, the Doppler ultrasound signal can be filtered, e.g. using a low pass filter. The principal purpose of the low pass filtering is to remove fetal (and optionally maternal) heartbeat signal components; accordingly, the frequency cutoff for the low pass filter should be below the lowest credible fetal (and optionally maternal) pulse rates, e.g. on the order of 60-90 Hz in some non-limiting embodiments.

At 104, an envelope is calculated for each signal segment of the acquired Doppler ultrasound signal. Typically, the Doppler ultrasound signal is segmented into time segments (also sometimes referred to as episodes) for processing convenience. In some embodiments, segmentation also allows for adaptive threshold adjustment. In some examples, the Doppler ultrasound signal may be segmented into a plurality of signal segments, which may optionally be partially overlapping. In some non-limiting illustrative examples, each segment is 2 seconds in duration with 2000 samples/segment. Envelope calculation for each segment may, for example, employ rectification of the signal followed by a smoothing using a low pass filter, though more generally any envelope detector may be employed. It is contemplated to integrate the low pass filtering to remove the cardiac signal with the envelope detector.

At 106, a plurality of peaks are derived from the calculated envelope of the Doppler ultrasound signal segments. For example, each peak is a detected local maximum value in the calculated envelope. Each peak of the plurality of peaks is associated with the signal segment of the Doppler ultrasound signal containing the peak.

At 108, a density of the derived peaks is determined as a function of peak amplitude. In an illustrative approach, the density of the derived peaks is calculated as a function of a plurality of amplitude grids or bins. The calculated density can then be quantified as the number of peaks with amplitude in each amplitude grid or bin.

At 110, a fetal movement threshold is selected based on the calculated density. In one example, the fetal movement threshold is selected as the peak amplitude value for the amplitude grid or bin having a maximum density value.

At 112, the fetal movement threshold is used in fetal monitoring. To this end, a signal segment under test of the Doppler ultrasound signal from the fetus being monitored is filtered and enveloped analogously to operations 102, 104 and peaks detected analogous to operation 106, and the signal segment under test is determined to include a fetal movement by comparing the peaks associating with the envelope of the signal segment under test with the fetal movement threshold determined at 110. If the peaks in the signal segment under test at 112 exceed the fetal movement threshold, then the signal segment under test is determined to include a fetal movement.

Figure 2:
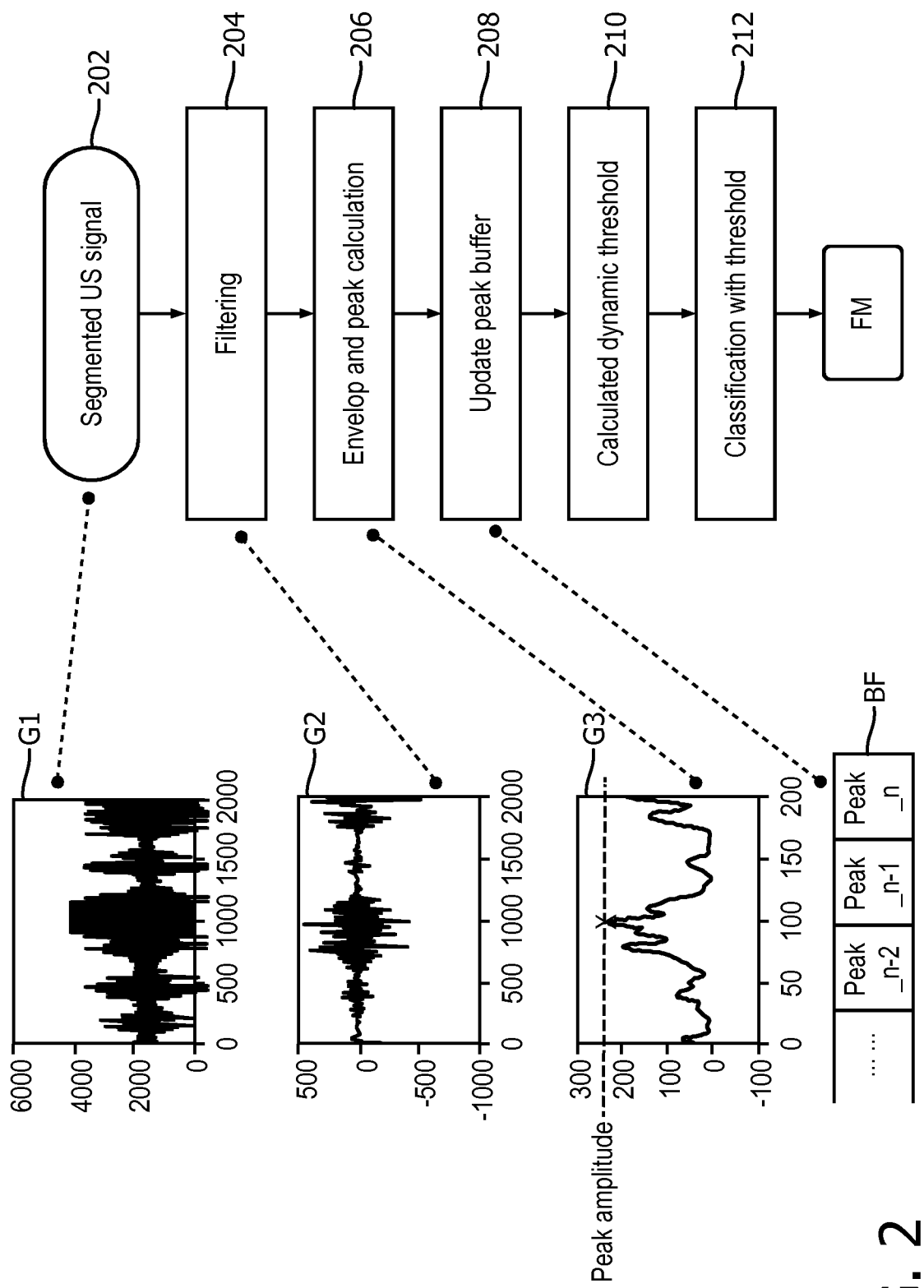
FIG. 2 diagrammatically shows a more detailed illustrative embodiment of processing of FIG. 1.

With reference now to FIG. 2, a more detailed illustrative embodiment of processing of FIG. 1 is described. In this illustrative example, every 0.25 second, a latest data segment or episode of the Doppler ultrasound signal is acquired at an operation 202. While 0.25 second segments are processed in illustrative FIG. 2, more generally the segments should be of sufficiently short duration to provide near real-time operation while being large enough to capture fetal movement episodes. At operation 204, the segment goes through pre-processing with a low pass filter to extract signal components predominantly containing fetal movement information. On the left-hand side of FIG. 2, the raw Doppler ultrasound signal is shown (graph G1) as well as the signal after low pass filtering (graph G2). In these graphs G1, G2 the x-axis plots one point generated every 0.25 s. The sampling rate is also 0.25 s for these points along the x-axis. A data segment of 2 s (with 2000 samples) of Doppler ultrasound signal is input to the calculation. The sampling rate for the Doppler ultrasound signal is 1 millisecond/sample. This is merely an illustrative example, and other segment sizes and sampling rates may be employed. In an operation 206, an envelope is calculated for the signal segment of the filtered data. At 208, the maximum peak is determined for each signal segment associated with the envelope. The graph G3 on the left-hand side in FIG. 2 shows an illustrative example of a calculated envelope and a peak marked by a cross, having a peak amplitude of about 240 in this example. In the graph G3 the scale is 0-200 due to down-sampling to a $1/10^{th}$ sampling rate. At 208, this peak amplitude is added to a peak buffer. An illustrative peak buffer is diagrammatically shown as representation BF on the left-hand side of FIG. 2, and is a buffer with a fixed time length of (by way of non-limiting example) 100 containing a history of peak amplitudes for each 0.25 second time segment.

Figure 3:
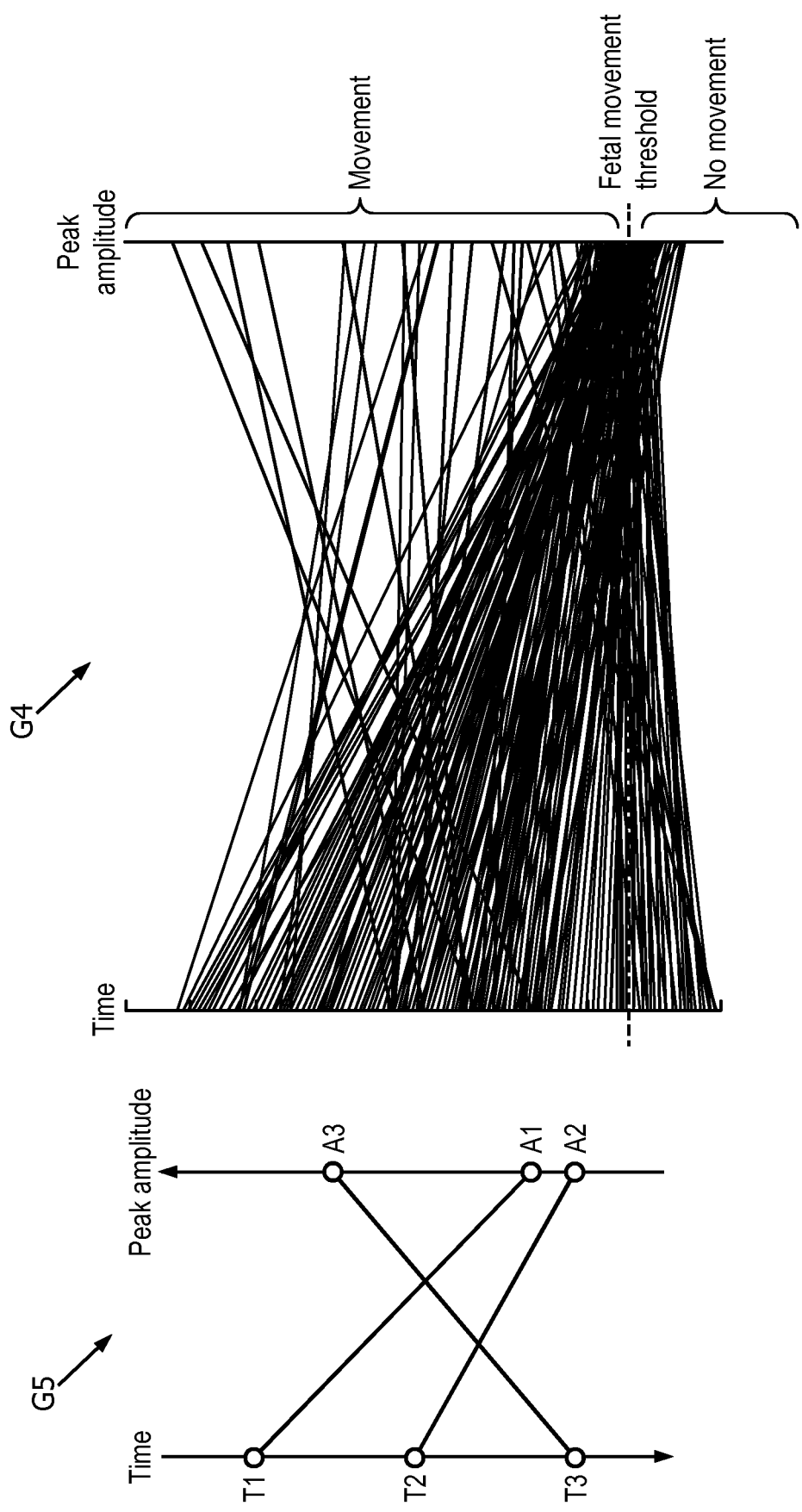
FIG. 3 diagrammatically shows for explanatory purposes parallel coordinates graphs illustrating the fetal movement threshold selection operation of FIGS. 1 and 2.

With continuing reference to FIG. 2 and with further reference to FIG. 3, in an operation 210 shown in FIG. 2 the fetal movement threshold is computed or updated based on the peaks in the peak buffer BF. In general, the fetal movement threshold is determined as the peak amplitude have the highest density of peaks observed in the peak buffer BF. For explanatory purposes, selection of the fetal movement threshold is diagrammatically illustrated using a parallel coordinates graph G4 shown in FIG. 3. A simplified illustrative example of the parallel coordinates graph is shown as diagrammatic example G5 which plots data for only three peaks. In the illustrative parallel coordinates graph, the peak amplitude data for each Doppler ultrasound signal segment envelope is plotted on parallel axes with one parallel axis representing the time and the other parallel axis representing peak amplitude. This is best seen in the simplified graph G5 which shows only three peaks at times T1, T2, T3 with corresponding respective peak amplitudes A1, A2, A3. As best seen in parallel coordinates graph G4 showing the data for an entire peak buffer BF (e.g., for 100 time segments in the illustrative example), the peak amplitude axis exhibits a region of highest density, that is, a region having a largest number of peak amplitudes. The peak amplitude with the highest density of peaks is selected as the fetal movement threshold, as indicated on graph G4. It was empirically found that using this peak amplitude at which the highest number of peaks are observed as the fetal movement threshold serves as an optimal choice for the fetal movement threshold because labeling of peaks as fetal movements or not fetal movements using this choice of threshold provided better agreement with ground truth information, e.g. as indicated by the mother, as compared with a higher or lower threshold. Further advantageously, this choice of threshold is readily derived from the Doppler ultrasound signal itself, in real-time during fetal monitoring, as disclosed herein.

FIG. 3 provides a conceptual illustration of the selection of the fetal movement threshold has the peak amplitude with highest peak density in the peak buffer BF. The operation 210 of FIG. 2 is generally not implemented using a parallel coordinates graph, but rather is implemented algorithmically using data of the peak buffer BF, for example suitably stored as data points [TS, AMP] where "TS" denotes the time stamp of the peak and "AMP" denotes the amplitude of the peak. In one approach, these data points are binned into different amplitude grids or bins, and the amplitude grid or bin with the highest count of data points (that is, the highest number of peaks falling in that peak amplitude bin) is selected as the threshold. The bin widths are chosen to provide a desired resolution for the fetal movement threshold (smaller bin widths provide higher resolution) while being wide enough to suppress noise due to the limited number of data points.

This is merely one illustrative algorithmic approach for determining the peak amplitude of highest peak density, and other algorithmic approaches are contemplated. For example, in another approach, a kernel density estimate (KDE) of peak density versus peak amplitude may be computed and the fetal movement threshold selected as the peak amplitude at which the KDE exhibits its largest value. In the KDE approach, each data point (i.e. peak) is represented by a Gaussian kernel (or other chosen kernel function) centered at the peak amplitude and having a chosen variance along the peak amplitude axis, and these Gaussians are summed and normalized to generate the KDE.

With continuing reference to FIGS. 2 and 3, at 212 the fetal movement threshold selected at 210 is used to classify peaks as being due to fetal movements or not due to fetal movements. As diagrammatically indicated in the parallel coordinates graph G4 of FIG. 3, any peak of a signal segment under test whose amplitude is above the selected fetal movement threshold is counted as a fetal movement, while any peak of a signal segment under test whose amplitude is below the selected fetal movement threshold is discarded.

Advantageously, the fetal movement threshold may optionally be adjusted dynamically for the particular fetus being monitored. In this approach, the Doppler ultrasound signal 202 is a portion of a Doppler ultrasound signal acquired for the fetus being monitored, and the fetal movement threshold is adaptively tuned by iterating the steps 204, 206, 208, 210 as Doppler ultrasound data is collected. To start the threshold adaptation process, a hard coded default fetal movement threshold may be initially used, and this default threshold is adjusted (i.e. adapted) over time for the particular fetus being monitored. In one adaptation approach, once a sufficient time interval of Doppler ultrasound signal is acquired by repeating steps 204, 206, 208 for successively acquired Doppler ultrasound signal segments (e.g. enough to fill the peak buffer BF) the fetal movement threshold is then determined by executing step 210 applied to the full peak buffer BF. Thereafter, the fetal movement threshold output by step 210 may be fixed for future fetal movement detection. Alternatively, the threshold can be determined dynamically and made more precise over time based on larger number of samples or more recent samples.

For example, the peak buffer BF may be treated as a first in-first out (FIFO) buffer so that the oldest peak data are discarded as newer peak data are added to the buffer BF, and the operation 210 applied occasionally to the current contents of the peak buffer BF to adaptively update the fetal movement threshold.

In another contemplated approach, which is not adaptive, training Doppler ultrasound signal data may be acquired from a cohort of fetal patients that are expected to be representative of typical fetuses. This training Doppler ultrasound signal data serves as the ultrasound signal 202 to which operations 204, 206, 208, 210 are applied to generate the fetal movement threshold. This "trained" threshold is then hard coded into the software of a Doppler ultrasound device for use in operation 212 which in this embodiment is performed on a fetus being clinically monitored (who is typically not part of the training cohort) to assess fetal movement of the clinically monitored fetus.

Figure 4:
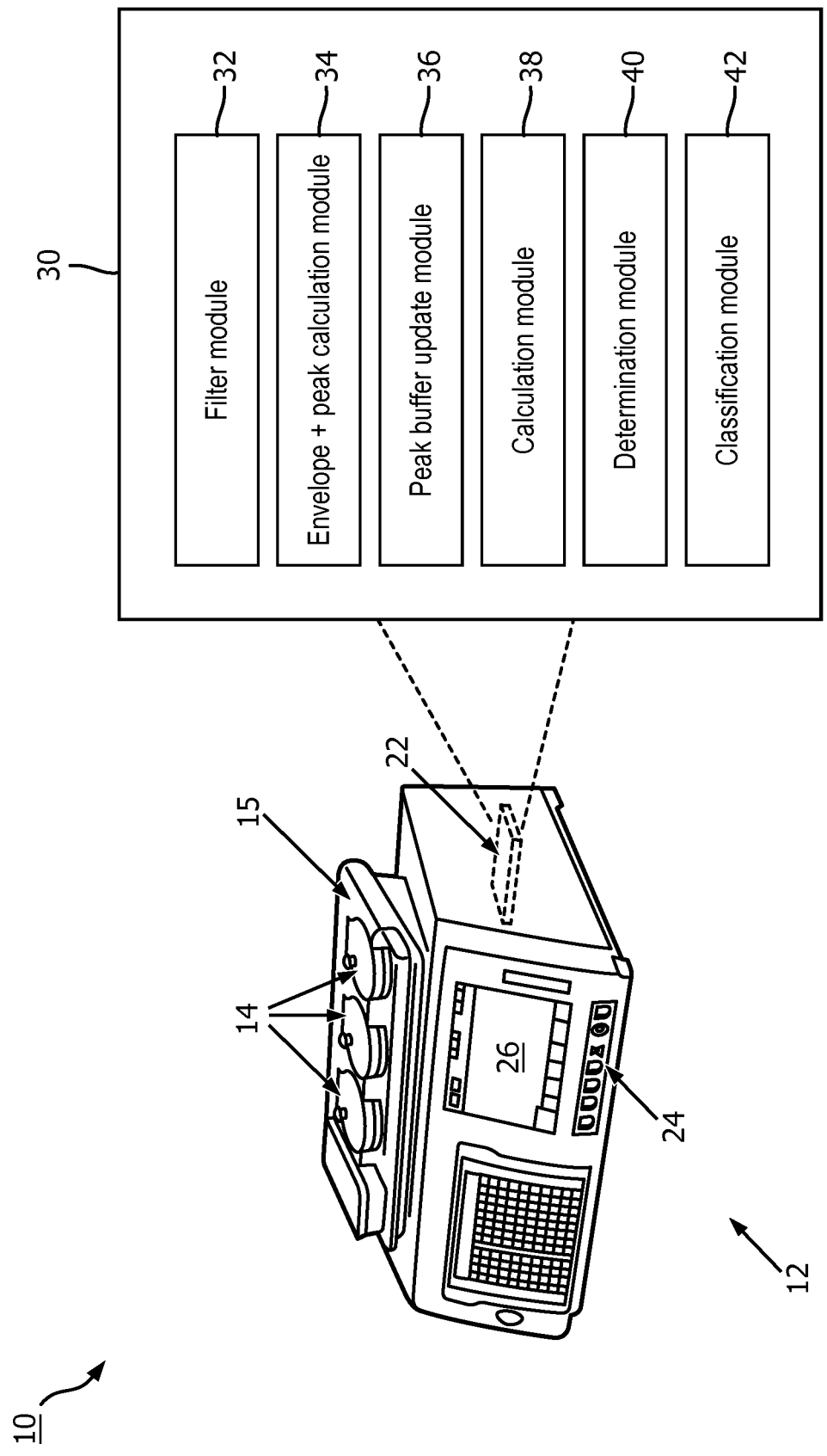
FIG. 4 shows an illustrative Doppler ultrasound device suitable for performing the fetal movement detection of FIG. 1 or FIG. 2.

With reference to FIG. 4, an illustrative Doppler fetal monitoring device or system 10 configured to detect fetal movements using the method of FIG. 1 or FIG. 2 is shown. As shown in FIG. 4, the device 10 includes a Doppler ultrasound device 12 including an ultrasonic transducer 14. FIG. 4 illustrates three transducers 14 disposed on a tray or receptacle 15 so as to be conveniently available with the Doppler ultrasound device 12 in a maternity ward or other medical setting likely to have multiple patients). The ultrasonic transducer 14 is configured to acquire a Doppler ultrasound signal. For example, the ultrasound device 12 can be secured or otherwise attached to an abdominal area of a mother (not shown) carrying a fetus (not shown) such that the ultrasonic transducer 14 overlies a portion of the fetus (e.g., the fetus and the transducer are separated by the abdominal area of the mother). Some non-limiting illustrative examples of suitable Doppler ultrasound devices include the Philips Avalon™ series fetal monitors with associated wired or wireless ultrasound transducer accessories.

The Doppler ultrasound device 12 further includes typical components, such as at least one electronic processor 22 (e.g. a microprocessor or microcontroller and ancillary electronics comprising an internal component diagrammatically indicated in phantom in the illustrative embodiment of FIG. 4), various user-operable controls 24 for performing setup and control of a monitoring session, and a display device or component 26. In some embodiments, the display device 26 can be a separate component from the Doppler ultrasound device 12 with a wired or wireless operational connection. The display device 26 can display ultrasound images, and for the purpose of fetal movement monitoring also displays information on fetal movements detected at operation 112 of FIG. 1 or operation 212 of FIG. 2. Fetal movement information may be displayed in various ways, such as a count of fetal movements over a defined time interval, which may be rolling in time (e.g., displaying the number of fetal movements detected in the last three minutes).

The at least one electronic processor 22 is operatively connected with a non-transitory storage medium (not shown) that stores instructions which are readable and executable by the at least one electronic processor 22 to perform a fetal movement detection method or process 30 including peak density-based adaptive adjustment of the fetal movement threshold as disclosed herein, e.g. employing the method of FIG. 1 or FIG. 2. The non-transitory storage medium may, for example, comprise a hard disk drive or other magnetic storage medium; a solid state drive, flash drive, electronically erasable programmable read-only memory (EEPROM) or other electronic memory storing firmware of the Doppler ultrasound device 12; an optical disk or other optical storage; various combinations thereof; or so forth. The non-transitory storage medium may store one or modules to perform the operations shown in FIGS. 1 and 2. For example, the non-transitory storage medium can include a filter module 32 programmed to filter the Doppler ultrasound signal (as described in operations 102 and 204); an envelope and peak calculation module 34 programmed calculate the envelope from the filtered Doppler ultrasound signal (as described in operations 104 and 206) and to determine peaks in the Doppler ultrasound signal from the envelope (as described in operation 106); a peak buffer update module 36 programmed to add the determined maximum peak to the peak buffer (as described in operation 208); a calculation module 38 programmed to calculate the density of peaks from the amplitudes of the derived peaks (as described in operation 108); a determination module 40 programmed to determine the dynamic fetal movement threshold from the calculated density (as described in operations 110 and 210); and a classification module 42 programmed to classify peaks as "movement" or "no movement" based on the determine fetal movement threshold (as described in operations 112 and 212). While in the illustrative example the on-board processor 22 of the Doppler ultrasound device 12 performs the fetal movement detection method or process 100 of FIG. 1, in other contemplated embodiments the fetal movement detection method or process 100 of FIG. 1 may be performed by cloud processing executing on a processor operatively connected via the Internet and/or a hospital data network or the like. In addition, the methods 100 and/or 200 may be implemented by software (e.g., a computer program or non-transitory computer program product), hardware (e.g., a hard disk drive or other magnetic storage medium; a solid state drive, flash drive, electronically erasable programmable read-only memory (EEPROM) or other electronic memory storing firmware; an optical disk or other optical storage; various combinations thereof), or a combination thereof.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A method of detecting fetal movements tuned for a specific fetus, comprising:
deriving a plurality of peaks from a Doppler ultrasound signal received from the fetus, each peak of the plurality of peaks being associated with an envelope of one of a plurality of signal segments of the Doppler ultrasound signal;
calculating a density of the peaks as a function of a plurality of peak amplitude grids, the density indicating the number of peaks with amplitude in each amplitude grid;
selecting a fetal movement threshold, tuned to the specific fetus, as the peak amplitude of the peak amplitude grid at which the calculated density of the peaks is maximum; and
determining that a Doppler ultrasound signal segment under test includes a fetal movement for the specific fetus by comparing the amplitude of a peak associating with the envelope of the Doppler ultrasound signal segment under test with the fetal movement threshold.

2. The method of claim 1, further comprising:
segmenting the Doppler ultrasound signal into the plurality of signal segments.

3. The method of claim 2, wherein at least two neighboring signal segments among the plurality of segments overlap in time.

4. The method of claim 1, wherein the Doppler ultrasound signal segment under test is acquired from the same fetus as the Doppler ultrasound signal from which the plurality of peaks is derived.

5. The method of claim 2, wherein the deriving, calculating, and selecting are iterated to adaptively tune the fetal movement threshold to the fetus.

6. The method of claim 2, further comprising:
acquiring the Doppler ultrasound signal from which the plurality of peaks are derived from the fetus; and
storing the derived plurality of peaks in a peaks buffer including updating contents of the peaks buffer during the acquiring using first in first out updating;
wherein the deriving, calculating, and selecting are repeated as the contents of the peaks buffer are updated to adaptively tune the fetal movement threshold to the fetus.

7. A device for detecting fetal movements tuned for a specific fetus, the device comprising:
a Doppler ultrasound transducer for acquiring a Doppler ultrasound signal from the fetus; and
at least one processor programmed to:
derive a plurality of peaks from the Doppler ultrasound signal, each peak of the plurality of peaks being associated with an envelope of one of a plurality of signal segments of the Doppler ultrasound signal;
calculate a density of the peaks as a function of a plurality of peak amplitude grids, the density indicating the number of peaks with amplitude in each amplitude grid;
select a fetal movement threshold, tuned for the specific fetus, as the peak amplitude of the peak amplitude grid at which the calculated density of the peaks is maximum; and
determine that a Doppler ultrasound signal segment under test includes a fetal movement for the specific fetus by comparing the amplitude of a peak associating with the envelope of the Doppler ultrasound signal segment under test with the fetal movement threshold.

8. The device of claim 7, wherein the at least one electronic processor is further programmed to segment the Doppler ultrasound signal into the plurality of signal segments.

9. The device of claim 8, wherein at least two neighboring signal segments among the plurality of segments overlap in time.

10. The device of claim 7, wherein the at least one electronic processor is further programed to store the derived plurality of peaks in a peaks buffer including updating contents of the peaks buffer during the acquiring using first in first out updating and to repeat the segmenting, deriving, calculating, and selecting as the contents of the peaks buffer are updated to adaptively tune the fetal movement threshold to the fetus.

11. A non-transitory computer readable medium having stored thereon program code readable and executable by one or more electronic processors to perform operations comprising:
deriving a plurality of peaks from a Doppler ultrasound signal acquired from a fetus, each peak of the plurality of peaks being associated with an envelope of one of a plurality of signal segments of the Doppler ultrasound signal;

calculating a density of the peaks as a function of a plurality of peak amplitude grids, the density indicating the number of peaks with amplitude in each amplitude grid;

selecting a fetal movement threshold for the fetus as the peak amplitude of the peak amplitude grid at which the calculated density of the peaks is maximum; and determining that a Doppler ultrasound signal segment under test includes a fetal movement for the fetus by comparing the amplitude of a peak associating with from the envelope of the Doppler ultrasound signal segment under test with the fetal movement threshold.

12. The non-transitory computer readable medium of claim 11, wherein the program code is further configured to perform operations comprising:

segmenting the Doppler ultrasound signal into the plurality of signal segments.

13. The non-transitory computer readable medium of claim 12, wherein at least two neighboring signal segments among the plurality of segments overlap in time.

14. The non-transitory computer readable medium of claim 11, wherein the Doppler ultrasound signal segment under test is acquired from the same fetus as the Doppler ultrasound signal from which the plurality of peaks is derived.

15. The non-transitory computer readable medium of claim 12, wherein the operations of deriving, calculating, and selecting are iterated to adaptively tune the fetal movement threshold to the fetus.

16. The non-transitory computer readable medium of claim 12, wherein the program code is further configured to perform operations comprising:

acquiring the Doppler ultrasound signal from which the plurality of peaks are derived from the fetus; and storing the derived plurality of peaks in a peaks buffer including updating contents of the peaks buffer during the acquiring using first in first out updating;

wherein the deriving, calculating, and selecting operations are repeated as the contents of the peaks buffer are updated to adaptively tune the fetal movement threshold to the fetus.

* * * * *